US011833502B2

United States Patent
Zhang et al.

(10) Patent No.: US 11,833,502 B2
(45) Date of Patent: *Dec. 5, 2023

(54) COKE CONTROL REACTOR, AND DEVICE AND METHOD FOR PREPARING LOW-CARBON OLEFINS FROM OXYGEN-CONTAINING COMPOUND

(71) Applicant: DALIAN INSTITUTE OF CHEMICAL PHYSICS, CHINESE ACADEMY OF SCIENCES, Dalian (CN)

(72) Inventors: Tao Zhang, Dalian (CN); Mao Ye, Dalian (CN); Jinling Zhang, Dalian (CN); Shuliang Xu, Dalian (CN); Hailong Tang, Dalian (CN); Xiangao Wang, Dalian (CN); Cheng Zhang, Dalian (CN); Jinming Jia, Dalian (CN); Jing Wang, Dalian (CN); Hua Li, Dalian (CN); Chenggong Li, Dalian (CN); Zhongmin Liu, Dalian (CN)

(73) Assignee: DALIAN INSTITUTE OF CHEMICAL PHYSICS, CHINESE ACADEMY OF SCIENCES, Dalian (CN)

(*) Notice: Subject to any disclaimer, the term of this patent is extended or adjusted under 35 U.S.C. 154(b) by 0 days.

This patent is subject to a terminal disclaimer.

(21) Appl. No.: 17/784,649

(22) PCT Filed: Oct. 16, 2020

(86) PCT No.: PCT/CN2020/121560
§ 371 (c)(1),
(2) Date: Jun. 12, 2022

(87) PCT Pub. No.: WO2022/077457
PCT Pub. Date: Apr. 21, 2022

(65) Prior Publication Data
US 2023/0001370 A1 Jan. 5, 2023

(51) Int. Cl.
B01J 8/00 (2006.01)
B01J 8/18 (2006.01)
(Continued)

(52) U.S. Cl.
CPC ............. B01J 8/1809 (2013.01); B01J 8/005 (2013.01); B01J 8/1863 (2013.01); B01J 8/228 (2013.01);
(Continued)

(58) Field of Classification Search
CPC . B01J 29/90; B01J 8/005; B01J 8/1809; B01J 8/1863; B01J 8/228; B01J 8/24;
(Continued)

(56) References Cited

FOREIGN PATENT DOCUMENTS

| CN | 101279873 A | 10/2008 |
|---|---|---|
| CN | 202478902 U | 10/2012 |

(Continued)

*Primary Examiner* — Sharon Pregler
(74) *Attorney, Agent, or Firm* — Bayramoglu Law Offices LLC (57) ABSTRACT

A coke control reactor, and a device and method for preparing low-carbon olefins from an oxygen-containing compound are provided. The coke control reactor includes a coke control reactor shell, a reaction zone I, and a coke controlled catalyst settling zone; a cross-sectional area at any position of the reaction zone I is less than that of the coke controlled catalyst settling zone; n baffles are arranged in a vertical direction in the reaction zone I; the n baffles divide the reaction zone I into m reaction zone I subzones; and a catalyst circulation hole is formed in each of the baffles, such that a catalyst flows in the reaction zone I in a preset manner. A catalyst charge in the present coke control reactor can be automatically adjusted, and an average residence time of a catalyst in the coke control reactor can be controlled by changing process operating conditions.

20 Claims, 2 Drawing Sheets

(51) Int. Cl.
*B01J 8/22* (2006.01)
*B01J 8/26* (2006.01)
*C07C 1/22* (2006.01)
*C10G 3/00* (2006.01)

(52) U.S. Cl.
CPC .................. *B01J 8/26* (2013.01); *C07C 1/22* (2013.01); *C10G 3/60* (2013.01); *B01J 2208/0084* (2013.01); *B01J 2208/00707* (2013.01); *B01J 2208/00761* (2013.01); *B01J 2208/00938* (2013.01); *B01J 2208/00991* (2013.01); *C07C 2529/85* (2013.01); *C10G 2300/4075* (2013.01)

(58) Field of Classification Search
CPC ..... B01J 8/26; C07C 1/20; C07C 1/22; C07C 11/02; C10G 3/60
See application file for complete search history.

(56) References Cited

FOREIGN PATENT DOCUMENTS

| | | | | |
|---|---|---|---|---|
| CN | 103649275 A | * | 3/2014 | ............ B01J 23/755 |
| CN | 104610006 A | | 5/2015 | |
| CN | 108786670 A | | 11/2018 | |
| CN | 110818521 A | | 2/2020 | |
| CN | 110818522 A | | 2/2020 | |
| CN | 111099945 A | | 5/2020 | |
| JP | 2017501989 A | | 1/2017 | |
| JP | 2017504654 A | | 2/2017 | |
| WO | 2015077142 A1 | | 5/2015 | |
| WO | 2015081489 A1 | | 6/2015 | |
| WO | WO-2015081489 A1 | * | 6/2015 | .............. B01J 29/90 |

* cited by examiner

COKE CONTROL REACTOR, AND DEVICE AND METHOD FOR PREPARING LOW-CARBON OLEFINS FROM OXYGEN-CONTAINING COMPOUND

CROSS REFERENCE TO THE RELATED APPLICATIONS

This application is the national phase entry of International Application No. PCT/CN2020/121560, filed on Oct. 16, 2020, the entire contents of which are incorporated herein by reference.

TECHNICAL FIELD

The present application relates to a coke control reactor, and a device and method for preparing low-carbon olefins from an oxygen-containing compound, and belongs to the field of chemical catalysis.

BACKGROUND

Methanol-to-olefin technology (MTO) mainly includes DMTO (methanol-to-olefin) technology of Dalian Institute of Chemical Physics, Chinese Academy of Sciences and MTO technology of UOP Company of the United States. In 2010, the Shenhua Baotou methanol-to-olefin plant using DMTO technology was completed and put into operation. This is the world's first industrial application of MTO technology. As of the end of 2019, 14 DMTO industrial plants have been put into production, with a total production capacity of about 8 million tons of low-carbon olefins per year.

In recent years, DMTO technology has been further developed, and a new generation of DMTO catalyst with better performance have gradually begun industrial applications, creating higher benefits for DMTO plants. The new generation of DMTO catalyst has higher methanol processing capacity and low-carbon olefin selectivity. It is difficult for the existing DMTO industrial devices to take full advantage of the advantages of the new generation of DMTO catalyst. Therefore, it is necessary to develop a DMTO device and production method that can meet the needs of a new generation of DMTO catalyst with high methanol processing capacity and high selectivity of low-carbon olefins.

SUMMARY

According to an aspect of the present application, a coke control reactor is provided, which can achieve the on-line modification of a DMTO catalyst; and the modification in the present application refers to controlling the coke content, coke content distribution, and coke species in the DMTO catalyst to improve the activity of the DMTO catalyst and the selectivity for low-carbon olefins.

A major characteristic of a DMTO catalyst is that the low-carbon olefin selectivity in a methanol conversion process increases with the increase of a coke content in the catalyst. The low-carbon olefins mentioned in the present application refer to ethylene and propylene.

The applicants have found through research that main factors affecting the activity of a DMTO catalyst and the selectivity for low-carbon olefins include coke content, coke content distribution, and coke species in the catalyst. Under the same average coke content in catalysts, the narrower the coke content distribution, the higher the selectivity and activity of low-carbon olefins. Coke species in a catalyst may include polymethyl aromatic hydrocarbon compounds, polymethyl cycloalkanes, and the like, where polymethylbenzene and polymethylnaphthalene can promote the formation of ethylene. Therefore, the control of the coke content, coke content distribution, and coke species in a catalyst is the key to control the activity of the DMTO catalyst and improve the selectivity of low-carbon olefins.

According to a first aspect of the present application, a coke control reactor is provided, where the coke control reactor includes a coke control reactor shell, a reaction zone I, and a coke controlled catalyst settling zone;

the coke control reactor shell includes an upper coke control reactor shell and a lower coke control reactor shell;

the upper coke control reactor shell encloses the coke controlled catalyst settling zone;

the lower coke control reactor shell encloses the reaction zone I;

the reaction zone I communicates with the coke controlled catalyst settling zone;

a cross-sectional area at any position of the reaction zone I is less than a cross-sectional area at any position of the coke controlled catalyst settling zone;

n baffles are arranged in a vertical direction in the reaction zone I, bottoms of the n baffles are connected to a bottom of the coke control reactor, tops of the n baffles are located in the coke controlled catalyst settling zone, and the n baffles divide the reaction zone I into m reaction zone I subzones, where m and n are both integers; and a catalyst circulation hole is formed in each of the baffles, such that a catalyst flows in the reaction zone I in a preset manner.

Optionally, $1 \leq n \leq 9$; and $2 \leq m \leq 10$.

Optionally, cross sections of the reaction zone I and the reaction zone I subzones may be all rectangular; a catalyst circulation hole may be formed in each of the n baffles; and catalyst circulation holes on adjacent baffles may be staggered up and down, such that a catalyst flows in the reaction zone I in a polyline manner.

Optionally, a cross section of the reaction zone I may be circular; a cross section of each of the reaction zone I subzones may be fan-shaped; and at least one catalyst circulation hole may be formed in each of n−1 of the baffles, such that a catalyst flows in the reaction zone I in an annular manner.

Optionally, a cross section of the reaction zone I may be annular; a cross section of each of the reaction zone I subzones may be fan-shaped; and at least one catalyst circulation hole may be formed in each of n−1 of the baffles, such that a catalyst flows in the reaction zone I in an annular manner.

Optionally, when cross sections of the reaction zone I and the reaction zone I subzones in the present application are all rectangular, n baffles may be arranged in the reaction zone I, and the n baffles may divide the reaction zone I into n+1 reaction zone I subzones, that is, m=n+1.

Optionally, when a cross section of the reaction zone I in the present application is circular, n baffles may be arranged in the reaction zone I, and the n baffles may divide the reaction zone I into n reaction zone I subzones, that is, m=n; and a diameter of the coke controlled catalyst settling zone may be larger than a diameter of the reaction zone I.

Optionally, when a cross section of the reaction zone I in the present application is annular, n baffles may be arranged in the reaction zone I, and the n baffles may divide the reaction zone I into n reaction zone I subzones, that is, m=n; a cylinder may be arranged in a center of the reaction zone I, and the baffles may be connected to a side wall of the cylinder, such that the cross section of each of the reaction zone I subzones is sector-annular; and a diameter of the coke controlled catalyst settling zone may be larger than a diameter of the reaction zone I.

Optionally, a cross-sectional area of the coke controlled catalyst settling zone may be 1.5 to 3 times a cross-sectional area of the reaction zone I.

Specifically, one or more catalyst circulation holes can be formed in each of the baffles, which is not strictly limited in the present application. When a plurality of catalyst circulation holes are formed, relative positions of the catalyst circulation holes are not strictly limited in the present application. For example, the plurality of catalyst circulation holes may be arranged in parallel, or may be arranged randomly.

Optionally, the coke control reactor may further include a transition zone;

the transition zone may be located between the reaction zone I and the coke controlled catalyst settling zone;

a cross-sectional area at any position of the transition zone may be between the cross-sectional area at any position of the reaction zone I and the cross-sectional area at any position of the coke controlled catalyst settling zone; and the transition zone, the reaction zone I, and the coke controlled catalyst settling zone may communicate with each other coaxially.

Specifically, the transition zone in the present application may be configured to connect the reaction zone I and the coke controlled catalyst settling zone.

Optionally, upper ends of the baffles in the present application may be located in the transition zone, and lower ends of the baffles may be connected to a bottom of the reaction zone I.

Optionally, the coke control reactor may be a bubbling fluidized bed reactor.

Optionally, the reaction zone I may include a catalyst inlet, a coke controlled catalyst outlet, and a coke control raw material inlet;

the m reaction zone I subzones may include a $1^{st}$ reaction zone I subzone, and a $2^{nd}$ reaction zone I subzone to an $m^{th}$ reaction zone I subzone; the catalyst inlet may be formed in the $1^{st}$ reaction zone I subzone; the coke controlled catalyst outlet may be formed in the $m^{th}$ reaction zone I subzone;

the coke control raw material inlet may be formed at a bottom of each of the reaction zone I subzones;

the coke controlled catalyst settling zone may include a coke control gas outlet; and the coke control gas outlet may be formed at a top of the coke controlled catalyst settling zone.

Preferably, a coke control reactor distributor may be provided at the coke control raw material inlet for feeding a coke control raw material.

Optionally, a coke control product gas delivery pipe may be provided at the coke control gas outlet.

Optionally, a coke control reactor distributor may be provided at a bottom of each of the reaction zone I subzones. In this way, the coke control raw material can enter the reaction zone I uniformly as a whole, such that the phenomenon of non-uniform distribution of the coke control raw material among the subzones can be avoided, and the narrow coke content distribution in a catalyst can be well achieved.

Optionally, a coke controlled catalyst delivery pipe may be provided at the coke controlled catalyst outlet for delivering a coke controlled catalyst to the reaction zone II.

In the present application, a shape of the coke controlled catalyst delivery pipe is not strictly limited, as long as it is ensured that the coke controlled catalyst delivery pipe can deliver a coke controlled catalyst to the reaction zone. For example, the coke controlled catalyst delivery pipe can be a long pipe with a bent structure, and can also be in other suitable shapes.

Optionally, a coke controlled catalyst slide valve may be further provided on the coke controlled catalyst delivery pipe for controlling the circulation of a catalyst.

In the present application, baffles with circulation holes are arranged in the reaction zone I to divide the coke control zone into a plurality of reaction zone I subzones, such that a catalyst can flow regularly in the reaction zone I, which controls a residence time of a catalyst entering the reaction zone I and a coke control mode to enable a narrow coke content distribution in the catalyst and control the coke species and coke content in the catalyst. The low uniformity of coke content on catalyst granules is avoided, that is, some catalyst granules have a low coke content, and some catalyst granules have a high coke content, resulting in a wide coke content distribution in the catalyst.

In the present application, the catalyst entering the coke control zone may be a fresh catalyst or a regenerated catalyst. Preferably, the catalyst may be a regenerated catalyst, such that both the regeneration and the coke control can be achieved on-line.

According to a second aspect of the present application, a method for on-line modification of a DMTO catalyst is provided, which is implemented using the above-mentioned coke control reactor.

Optionally, the method may at least include feeding a catalyst and a coke control raw material into the reaction zone I to allow a reaction to generate a product with a coke controlled catalyst, where the catalyst flows in a preset manner through the catalyst circulation holes on the baffles.

Optionally, the coke control raw material may include $C_1$-$C_6$ hydrocarbon compounds.

Preferably, the hydrocarbon compounds may be at least one from the group consisting of $C_1$-$C_6$ alkanes and $C_1$-$C_6$ olefins.

Optionally, a reaction temperature of the coke control reaction may be 300° C. to 700° C.

Optionally, the coke control reactor in the present application may be a bubbling fluidized bed reactor.

Optionally, the coke control raw material may further include at least one from the group consisting of hydrogen, alcohol compound, and water; and a proportion of a total mass of the alcohol compound and the water in a mass of the coke control raw material may be greater than or equal to 10% and less than or equal to 50%; and preferably, the alcohol compound may be at least one from the group consisting of methanol and ethanol.

Optionally, the coke control raw material may include 0 wt % to 20 wt % of hydrogen, 0 wt % to 50 wt % of methane, 0 wt % to 50 wt % of ethane, 0 wt % to 20 wt % of ethylene, 0 wt % to 50 wt % of propane, 0 wt % to 20 wt % of propylene, 0 wt % to 90 wt % of butane, 0 wt % to 90 wt % of butene, 0 wt % to 90 wt % of pentane, 0 wt % to 90 wt % of pentene, 0 wt % to 90 wt % of hexane, 0 wt % to 90 wt % of hexene, 0 wt % to 50 wt % of methanol, 0 wt % to 50 wt % of ethanol, and 0 wt % to 50 wt % of water; and a content of the hydrocarbon compounds may be greater than 0%.

Optionally, the catalyst may include an SAPO-34 molecular sieve; a coke content in the catalyst may be less than or equal to 3 wt %;

a coke content in the coke controlled catalyst may be 4 wt % to 9 wt %;

a quartile deviation of a coke content distribution in the coke controlled catalyst may be less than 1 wt %;

preferably, coke species in the coke controlled catalyst may include polymethylbenzene and polymethylnaphthalene;

a total mass of the polymethylbenzene and the polymethylnaphthalene may account for greater than or equal to 70 wt % of a total mass of coke;

a mass of coke species with a molecular weight greater than 184 may account for less than or equal to 25 wt % of the total mass of coke; and the total mass of coke may refer to a total mass of coke species.

Specifically, in the present application, the coke content in the coke controlled catalyst is controlled at 4 wt % to 9 wt % through the arrangement of the reaction zone I and the selection of the coke control process. Since the catalyst is powdery, the coke content in the catalyst refers to an average coke content in catalyst granules, but coke contents in different catalyst granules may actually be different. In the present application, the quartile deviation of the coke content distribution in the coke controlled catalyst granules can be controlled to be less than 1 wt %, such that the overall coke content distribution of the catalyst is narrow, thereby improving the activity of the catalyst and the selectivity for low-carbon olefins.

In the present application, types and contents of coke species are also very important, which is also one of the objectives of control in the present application. In the present application, a total mass of the polymethylbenzene and the polymethylnaphthalene is controlled to be greater than or equal to 70 wt % of the total mass of coke through the arrangement of coke control and the selection of coke control process parameters to improve the activity of the catalyst and the selectivity for low-carbon olefins.

Optionally, process operating conditions of the reaction zone I of the coke control reactor may be as follows: apparent gas linear velocity: 0.1 m/s to 0.5 m/s; reaction temperature: 300° C. to 700° C.; reaction pressure: 100 kPa to 500 kPa; and bed density: 400 kg/m$^3$ to 800 kg/m$^3$.

Optionally, the method may include: feeding a coke control raw material and a catalyst into the reaction zone I to allow a reaction to generate a coke controlled catalyst and a coke control product gas; allowing the coke controlled catalyst to pass through the m reaction zone I subzones in sequence through the catalyst circulation holes on the baffles and then flow out through the coke controlled catalyst outlet; and allowing the coke control product gas to flow out through the coke control gas outlet.

According to a third aspect of the present application, a device for preparing low-carbon olefins from an oxygen-containing compound is provided, including a methanol conversion reactor and the coke control reactor described above.

Optionally, the methanol conversion reactor may include a methanol conversion reactor shell and a delivery pipe;

the methanol conversion reactor shell may include a lower methanol conversion reactor shell and an upper methanol conversion reactor shell;

the lower methanol conversion reactor shell may enclose a reaction zone II;

the delivery pipe may be located above the reaction zone II; the delivery pipe may have one end closed and the other end communicating with the reaction zone II;

the upper methanol conversion reactor shell may be arranged on a periphery of the delivery pipe;

the upper methanol conversion reactor shell and a pipe wall of the delivery pipe may enclose a cavity;

the cavity may be divided into a spent catalyst zone and a gas-solid separation zone from bottom to top, respectively; and the spent catalyst zone may be provided with a spent catalyst zone gas distributor.

Optionally, a bottom of the reaction zone II may be provided with a methanol conversion reactor distributor, Optionally, the spent catalyst zone may be further provided with a methanol conversion reactor cooler, and the methanol conversion reactor cooler may be located above the spent catalyst zone gas distributor and below the gas-solid separation zone.

Optionally, the coke control product gas delivery pipe may communicate with the gas-solid separation zone, and may be configured to deliver a coke control product gas to the gas-solid separation zone.

Optionally, the gas-solid separation zone may be provided with a first gas-solid separation unit of the methanol conversion reactor;

an upper part of the delivery pipe may be connected to an inlet of the first gas-solid separation unit of the methanol conversion reactor;

a spent catalyst outlet of the first gas-solid separation unit of the methanol conversion reactor may be formed in the spent catalyst zone;

a gas outlet of the first gas-solid separation unit of the methanol conversion reactor may communicate with a methanol conversion reactor gas collection chamber; and the methanol conversion reactor gas collection chamber may communicate with a product gas delivery pipe.

Optionally, the gas-solid separation zone may be further provided with a second gas-solid separation unit of the methanol conversion reactor;

a gas inlet of the second gas-solid separation unit of the methanol conversion reactor may be formed in the gas-solid separation zone;

a spent catalyst outlet of the second gas-solid separation unit of the methanol conversion reactor may be formed in the spent catalyst zone; and a gas outlet of the second gas-solid separation unit of the methanol conversion reactor may communicate with the methanol conversion reactor gas collection chamber.

Optionally, the first gas-solid separation unit of the methanol conversion reactor may adopt one or more sets of gas-solid cyclone separators, and each set of gas-solid cyclone separators may include a first-stage gas-solid cyclone separator and a second-stage gas-solid cyclone separator.

Optionally, the second gas-solid separation unit of the methanol conversion reactor may adopt one or more sets of gas-solid cyclone separators, and each set of gas-solid cyclone separators may include a first-stage gas-solid cyclone separator and a second-stage gas-solid cyclone separator.

Optionally, the spent catalyst zone gas distributor may be located below the first gas-solid separation unit of the methanol conversion reactor and the second gas-solid separation unit of the methanol conversion reactor.

Optionally, a spent catalyst circulation pipe and a spent catalyst inclined pipe may be further arranged outside the spent catalyst zone;

the spent catalyst circulation pipe may be configured to connect the spent catalyst zone and the reaction zone II; and the spent catalyst inclined pipe may be configured to output a spent catalyst.

Optionally, the spent catalyst circulation pipe may be further provided with a spent catalyst circulation slide valve configured to control the circulation of a catalyst.

Optionally, one end of the spent catalyst circulation pipe may be connected to the reaction zone II, and may be located above the methanol conversion reactor distributor; and the other end may be connected to the spent catalyst zone.

Optionally, the reaction zone II may communicate with the reaction zone I through a coke controlled catalyst delivery pipe.

Optionally, the device may further include a regenerator; the regenerator may be connected to the spent catalyst inclined pipe, such that a spent catalyst is able to be delivered to the regenerator;

the regenerator may be connected to a regenerated catalyst delivery pipe, such that a regenerated catalyst is able to be delivered to the coke control reactor; and an inner bottom of the regenerator may be provided with a regenerator distributor.

Optionally, a bottom of the regenerator may be further provided with a regenerator stripper;

an upper section of the regenerator stripper may be arranged inside the regenerator, and an inlet of the upper section of the regenerator stripper may be formed above the regenerator distributor; and a lower section of the regenerator stripper may be arranged outside the regenerator, and an outlet of the lower section of the regenerator stripper may be connected to the regenerated catalyst delivery pipe.

Optionally, the regenerator may include a regenerator shell and a regenerator stripper; a lower section of the regenerator stripper may be arranged outside the regenerator shell, and an outlet of the lower section of the regenerator stripper may be connected to the regenerated catalyst delivery pipe. An upper section of the regenerator stripper may be arranged inside the regenerator shell, and an inlet of the upper section of the regenerator stripper may be formed above the regenerator distributor.

Optionally, the regenerator may be connected to the spent catalyst inclined pipe through a spent catalyst delivery pipe and a methanol conversion reactor stripper; and the regenerator may be connected to the regenerated catalyst delivery pipe through the regenerator stripper.

Optionally, a spent catalyst slide valve may be further arranged between the methanol conversion reactor stripper and the spent catalyst delivery pipe.

Optionally, the regenerator may be further provided with a regenerator gas-solid separation unit and a regenerator gas collection chamber;

a regenerated catalyst outlet of the regenerator gas-solid separation unit may be formed above the regenerator distributor;

a gas outlet of the regenerator gas-solid separation unit may be connected to the regenerator gas collection chamber; and the regenerator gas collection chamber may be connected to a flue gas delivery pipe located outside the regenerator.

Optionally, the regenerator stripper may be further provided with a regenerator cooler.

Optionally, the regenerator gas-solid separation unit may adopt one or more sets of gas-solid cyclone separators, and each set of gas-solid cyclone separators may include a first-stage gas-solid cyclone separator and a second-stage gas-solid cyclone separator.

Optionally, a regenerated catalyst slide valve may be further arranged between the regenerator stripper and the regenerated catalyst delivery pipe.

According to a fourth aspect of the present application, a method for preparing low-carbon olefins from an oxygen-containing compound is provided, including the method for on-line modification of a DMTO catalyst described above.

Optionally, the method may further include: feeding a coke control product gas into a gas-solid separation zone of a methanol conversion reactor; and feeding a coke controlled catalyst into a reaction zone II of the methanol conversion reactor.

Optionally, in the reaction zone II, a raw material with an oxygen-containing compound may contact and react with the coke controlled catalyst to generate a stream A with low-carbon olefins and a spent catalyst.

Optionally, the stream A may be separated into a gas-phase stream B and a solid-phase stream C after being subjected to gas-solid separation in the gas-solid separation zone of the methanol conversion reactor;

the gas-phase stream B may enter a methanol conversion reactor gas collection chamber;

the solid-phase stream C may enter a spent catalyst zone; and the gas-phase stream B may include the low-carbon olefins, and the solid-phase stream C may include the spent catalyst.

Optionally, a spent catalyst zone fluidizing gas may be fed into the spent catalyst zone;

the spent catalyst zone fluidizing gas and a coke control product gas may be mixed and carry a part of the spent catalyst to produce a stream D;

the stream D may be separated into a gas-phase stream E and a solid-phase stream F after being subjected to gas-solid separation;

the gas-phase stream E may enter the methanol conversion reactor gas collection chamber; the solid-phase stream F may enter the spent catalyst zone;

the gas-phase stream E may be a mixed gas of the spent catalyst zone fluidizing gas and the coke control product gas; and the solid-phase stream F may be the spent catalyst.

Optionally, the gas-phase stream B and the gas-phase stream E may be mixed in the methanol conversion reactor gas collection chamber to produce a product gas, and the product gas may enter a downstream working section through a product gas delivery pipe.

Optionally, a part of the spent catalyst in the spent catalyst zone may be returned to a bottom of the reaction zone II through a spent catalyst circulation pipe; and the remaining part of the spent catalyst may be discharged through a spent catalyst inclined pipe.

Optionally, the spent catalyst discharged through the spent catalyst inclined pipe may be fed into a regenerator; and a regeneration gas may be fed into the regenerator to contact and react with the spent catalyst to obtain a stream G with a flue gas and a regenerated catalyst.

Optionally, the stream G may be subjected to gas-solid separation;

a separated flue gas may enter a regenerator gas collection chamber, and then enter a downstream flue gas treatment system through a flue gas delivery pipe; and a separated regenerated catalyst may be stripped and cooled, and then enter a coke control reactor.

Optionally, the oxygen-containing compound may include methanol and/or dimethyl ether (DME).

Optionally, a coke content in the spent catalyst may be 9 wt % to 13 wt %.

Optionally, the spent catalyst zone fluidizing gas may include nitrogen and/or water vapor.

Optionally, the regeneration gas may include 0 wt % to 100 wt % of air, 0 wt % to 50 wt % of oxygen, 0 wt % to 50 wt % of nitrogen, and 0 wt % to 50 wt % of water vapor.

Optionally, process operating conditions of the reaction zone II of the methanol conversion reactor may be as follows: apparent gas linear velocity: 0.5 m/s to 7.0 m/s; reaction temperature: 350° C. to 550° C.; reaction pressure: 100 kPa to 500 kPa; and bed density: 100 kg/m$^3$ to 500 kg/m$^3$.

Optionally, process operating conditions of the spent catalyst zone of the methanol conversion reactor may be as follows: apparent gas linear velocity: 0.1 m/s to 1.0 m/s; reaction temperature: 350° C. to 550° C.; reaction pressure: 100 kPa to 500 kPa; and bed density: 200 kg/m$^3$ to 800 kg/m$^3$.

Optionally, process operating conditions of the regenerator may be as follows: apparent gas linear velocity: 0.5 m/s to 2.0 m/s; regeneration temperature: 600° C. to 750° C.; regeneration pressure: 100 kPa to 500 kPa; and bed density: 150 kg/m$^3$ to 700 kg/m$^3$.

The $C_1$-$C_6$ hydrocarbon compounds in the present application refer to hydrocarbon compounds with 1 to 6 carbon atoms.

Possible beneficial effects of the present application:

(1) The coke control reactor in the present application is a bubbling fluidized bed reactor with m reaction zone subzones, where a height of a baffle between adjacent reaction zone subzones is higher than a height of a catalyst dense bed, and a catalyst can flow from an upstream subzone to a downstream subzone only through catalyst circulation holes in the baffles, such that, 1. a catalyst charge in the coke control reactor can be automatically adjusted (that is, an average residence time of a catalyst in the coke control reactor can be controlled by changing process operating conditions to control a coke content in the catalyst); and 2. a residence time distribution of a catalyst is controlled with the structure of m reaction zone subzones (the residence time distribution is similar to m serially-connected completely-mixed tank reactors), and thus a catalyst with a narrow coke content distribution can be obtained.

(2) The present application can control the conversion and generation of coke species in a catalyst. On the one hand, inactive large-molecule coke species remaining in a regenerated catalyst are converted into small-molecule coke species; and on the other hand, a coke control raw material can also enter the catalyst to generate highly-active small-molecule coke species, and the small-molecule coke species are mainly polymethylbenzene and polymethylnaphthalene, which can improve the selectivity for ethylene.

(3) With the method for on-line modification of a DMTO catalyst through a coke control reaction in the present application, a coke controlled catalyst with high coke content, narrow coke content distribution, and polymethylbenzene and polymethylnaphthalene as main coke species components can be obtained, that is, the regenerated catalyst with low selectivity for low-carbon olefins is converted into a coke controlled catalyst with high selectivity for low-carbon olefins.

(4) The regenerated catalyst in the present application can be directly used in the process of preparing low-carbon olefins from an oxygen-containing compound without a coke control treatment, and in this case, the selectivity for low-carbon olefins in an obtained product gas is 80 wt % to 83 wt %. When the regenerated catalyst in the present application is subjected to a coke control treatment and then used in the process of preparing low-carbon olefins from an oxygen-containing compound, the selectivity for low-carbon olefins in an obtained product gas is 93 wt % to 96 wt %.

(5) The methanol conversion reactor in the present application is a composite fluidized bed reactor including a fast fluidized bed zone and a bubbling fluidized bed zone. The fast fluidized bed zone is a reaction zone, which can obtain a high methanol flux, increase a methanol treatment capacity per unit volume of the device, and make a methanol weight hourly space velocity (WHSV) reach 5 h$^{-1}$ to 2 h$^{-1}$. The bubbling fluidized bed zone is a spent catalyst zone, which is configured to reduce a temperature of a spent catalyst, deliver a low-temperature spent catalyst to the reaction zone, increase a bed density of the reaction zone, and control a bed temperature of the reaction zone. When the apparent gas linear velocity is 0.5 m/s to 7.0 m/s, a corresponding bed density is 500 kg/m$^3$ to 100 kg/m$^3$.

(6) The methanol conversion reactor in the present application adopts a structure in which the first gas-solid separation unit of the methanol conversion reactor is directly connected to the delivery pipe, which realizes the rapid separation of a low-carbon olefin-containing gas and a spent catalyst in the stream A, and avoids that low-carbon olefins further react under the action of the spent catalyst to generate hydrocarbon by-products with a large molecular weight.

BRIEF DESCRIPTION OF THE DRAWINGS

Reference numerals in FIG. 1.

1 represents a coke control reactor; 1-1 represents a coke control reactor shell; 1-2 represents a coke control reactor distributor; 1-3 represents a baffle; 1-4 represents a coke controlled catalyst delivery pipe; 1-5 represents a coke controlled catalyst slide valve; 1-6 represents a coke control product gas delivery pipe; 2 represents a methanol conversion reactor; 2-1 represents a methanol conversion reactor shell; 2-2 represents a methanol conversion reactor distributor; 2-3 represents a delivery pipe; 2-4 represents a first gas-solid separation unit of the methanol conversion reactor; 2-5 represents a methanol conversion reactor gas collection chamber; 2-6 represents a spent catalyst zone gas distributor; 2-7 represents a methanol conversion reactor cooler; 2-8 represents a second gas-solid separation unit of the methanol conversion reactor; 2-9 represents a product gas delivery pipe; 2-10 represents a spent catalyst circulation pipe; 2-11 represents a spent catalyst circulation slide valve; 2-12 represents a spent catalyst inclined pipe; 2-13 represents a methanol conversion reactor stripper; 2-14 represents a spent catalyst slide valve; 2-15 represents a spent catalyst delivery pipe; 3 represents a regenerator; 3-1 represents a regenerator shell; 3-2 represents a regenerator distributor; 3-3 represents a regenerator gas-solid separation unit; 3-4 represents a regenerator gas collection chamber; 3-5 represents a flue gas delivery pipe; 3-6 represents a regenerator stripper; 3-7 represents a regenerator cooler; 3-8 represents a regenerated catalyst slide valve; and 3-9 represents a regenerated catalyst delivery pipe.

Reference numerals in FIG. 2.

1 represents a coke control reactor; 1-1 represents a coke control reactor shell; 1-3 represents a baffle; 1-4 represents a coke controlled catalyst delivery pipe; and 3-9 represents a regenerated catalyst delivery pipe.

Reference numerals in FIG. 3.

1 represents a coke control reactor; 1-1 represents a coke control reactor shell; 1-3 represents a baffle; 1-4 represents a coke controlled catalyst delivery pipe; and 3-9 represents a regenerated catalyst delivery pipe.

DETAILED DESCRIPTION OF THE EMBODIMENTS

The present application will be described in detail below with reference to examples, but the present application is not limited to these examples.

Unless otherwise specified, the raw materials and catalysts in the examples of the present application are all purchased from commercial sources.

The DMTO catalyst used in the examples of the present application is from Zhongke Catalysis (Dalian) Co., Ltd.

In order to improve the performance of a DMTO catalyst, the present application provides a method for on-line modification of a DMTO catalyst through a coke control reaction, including the following steps:

(a) a regenerated catalyst is delivered to a coke control reactor 1;

(b) a coke control raw material is delivered to a coke control reactor 1;

(c) the coke control raw material contacts and reacts with the regenerated catalyst in the coke control reactor 1, such that the coke control raw material is coked on the regenerated catalyst, where a coked catalyst is called a coke controlled catalyst; a coke content in the coke controlled catalyst is 4 wt % to 9 wt %; coke species include polymethylbenzene and polymethylnaphthalene, and a total mass of the polymethylbenzene and the polymethylnaphthalene accounts for greater than or equal to 70 wt % of a total mass of coke; and a mass of coke species with a molecular weight greater than 184 accounts for less than or equal to 25 wt % of the total mass of coke; and (d) the coke controlled catalyst is delivered to a methanol conversion reactor 2.

A reaction temperature of the coke control reaction may be 300° C. to 700° C.

Figure 1:
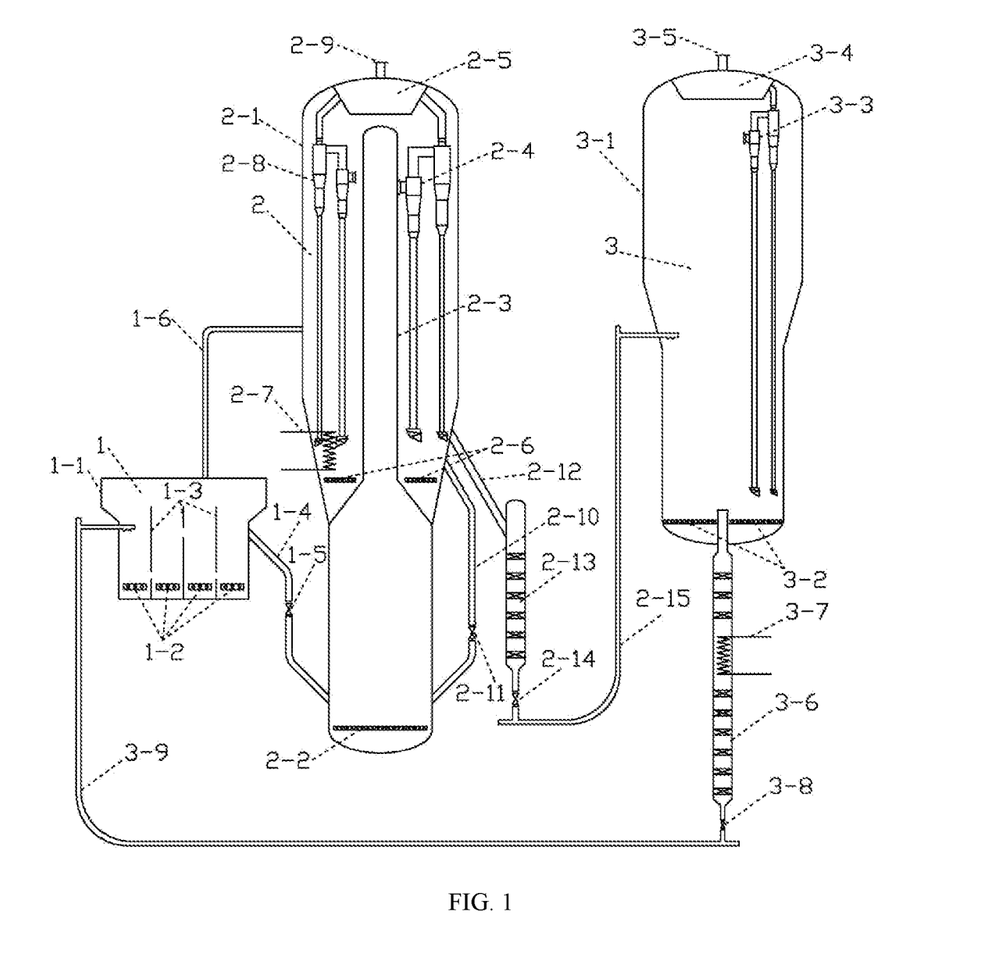
FIG. 1 is a schematic diagram of a DMTO device for preparing low-carbon olefins from an oxygen-containing compound according to an embodiment of the present application.

The present application also provides a method for preparing low-carbon olefins from an oxygen-containing compound that includes the method for on-line modification of a DMTO catalyst through a coke control reaction described above, and a device used thereby. The device includes a coke control reactor 1, a methanol conversion reactor 2, and a regenerator 3.

The coke control reactor 1 can realize the on-line modification of a DMTO catalyst through a coke control reaction, including: a coke control reactor shell 1-1, a coke control reactor distributor 1-2, a baffle 1-3, a coke controlled catalyst delivery pipe 1-4, a coke controlled catalyst slide valve 1-5, and a coke control product gas delivery pipe 1-6; the coke control reactor 1 is divided into a reaction zone I, a transition zone, and a coke controlled catalyst settling zone from bottom to top, respectively; n baffles 1-3 are arranged in the reaction zone I, bottoms of the baffles 1-3 are connected to a bottom of the coke controlled reactor shell 1-1, and tops of the baffles 1-3 are located in the transition zone, where n is an integer and $1 \leq n \leq 9$; the baffles 1-3 divide the reaction zone I into m reaction zone I subzones, where m is an integer and $2 \leq m \leq 10$; a bottom of each of the reaction zone I subzones is independently provided with a coke control reactor distributor 1-2, and m coke control reactor distributors 1-2 are arranged in the reaction zone I; an outlet of the regenerated catalyst delivery pipe 3-9 is connected to the $1^{st}$ reaction zone I subzone of the coke control reactor 1, and an inlet of the coke controlled catalyst delivery pipe 1-4 is connected to the $m^{th}$ reaction zone I subzone of the coke control reactor 1; a catalyst circulation hole is formed in each of the baffles 1-3, and catalyst circulation holes on adjacent upper and lower baffles 1-3 are staggered; a coke controlled catalyst slide valve 1-5 is arranged in the coke controlled catalyst delivery pipe 1-4, and an outlet of the coke controlled catalyst delivery pipe 1-4 is connected to a lower part of the methanol conversion reactor 2; and an inlet of the coke control product gas delivery pipe 1-6 is connected to a top of the coke control reactor 1, and an outlet of the coke control product gas delivery pipe 1-6 is connected to an upper part of the methanol conversion reactor 2.

In a preferred embodiment, a cross section of the reaction zone I of the coke control reactor 1 may be rectangular, a cross section of the reaction zone I subzone may be rectangular, and the $1^{st}$ to $m^{th}$ reaction zone I subzones may be arranged from left to right in sequence.

Figure 2:
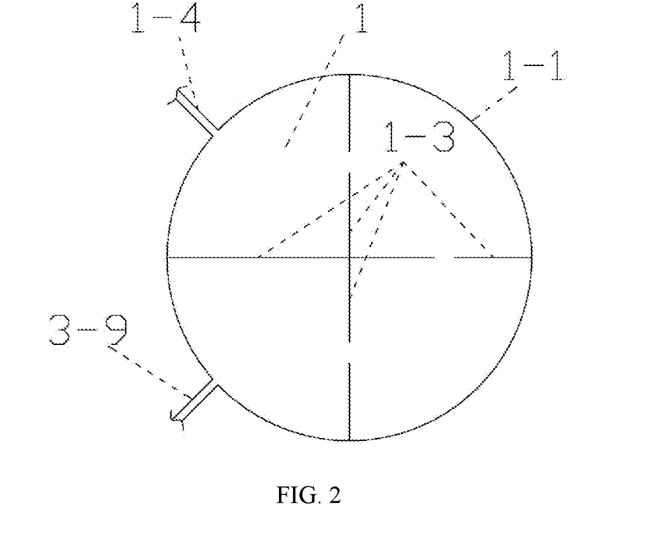
FIG. 2 is a schematic diagram of cross sections of a structure of the reaction zone of the coke control reactor of an embodiment of the present application, where a cross section of the reaction zone I of the coke control reactor of the embodiment is circular, and a cross section of a reaction zone subzone is fan-shaped; and the $1^{st}$ to $4^{th}$ reaction zone subzones are arranged concentrically in a counterclockwise direction, and a baffle shared by the $1^{st}$ reaction zone subzone and the $4^{th}$ reaction zone subzone of the coke control reactor does not have catalyst circulation holes.

In a preferred embodiment, a cross section of the reaction zone I of the coke control reactor 1 may be circular, and a cross section of a reaction zone I subzone may be fan-shaped; and the $1^{st}$ to $m^{th}$ reaction zone I subzones may be arranged concentrically in a clockwise or counterclockwise direction, and a baffle 1-3 shared by the $1^{st}$ reaction zone I subzone and the $m^{th}$ reaction zone I subzone of the coke control reactor 1 may not have catalyst circulation holes.

Figure 3:
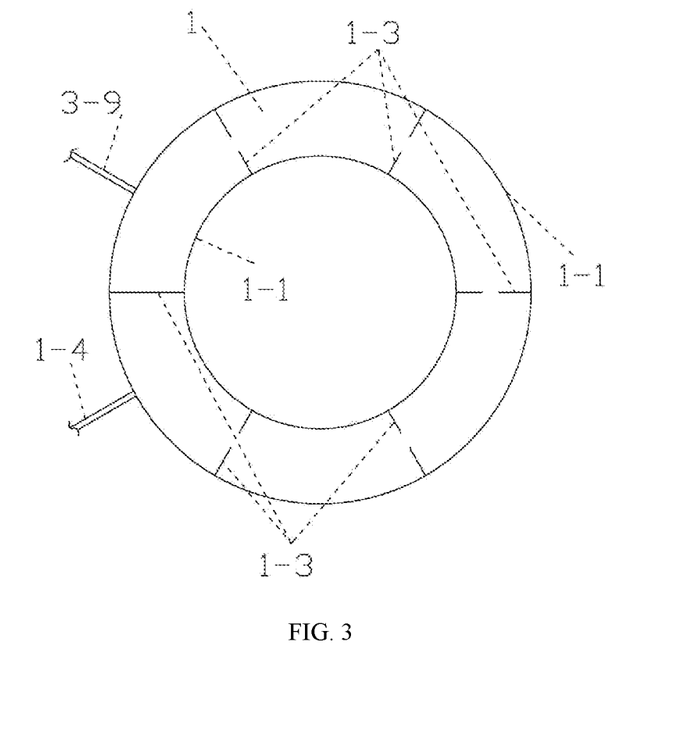
FIG. 3 is a schematic diagram of cross sections of a structure of the reaction zone of the coke control reactor of an embodiment of the present application, where a cross section of the reaction zone I of the coke control reactor of the embodiment is annular, and a cross section of a reaction zone subzone is sector-annular; and the $1^{st}$ to $6^{th}$ reaction zone subzones are arranged concentrically in a clockwise direction, and a baffle shared by the $1^{st}$ reaction zone subzone and the $6^{th}$ reaction zone subzone of the coke control reactor does not have catalyst circulation holes.

In a preferred embodiment, a cross section of the reaction zone I of the coke control reactor 1 may be annular, and a cross section of a reaction zone I subzone may be sector-annular; and the $1^{st}$ to $m^{th}$ reaction zone I subzones may be arranged concentrically in a clockwise or counterclockwise direction, and a baffle 1-3 shared by the $1^{st}$ reaction zone I subzone and the $m^{th}$ reaction zone I subzone of the coke control reactor 1 may not have catalyst circulation holes.

The coke control reactor 1 may be a bubbling fluidized bed reactor.

The methanol conversion reactor 2 includes a methanol conversion reactor shell 2-1, a methanol conversion reactor distributor 2-2, a delivery pipe 2-3, a first gas-solid separation unit 2-4 of the methanol conversion reactor, a methanol conversion reactor gas collection chamber 2-5, a spent catalyst zone gas distributor 2-6, a methanol conversion reactor cooler 2-7, a second gas-solid separation unit 2-8 of the methanol conversion reactor, a product gas delivery pipe 2-9, a spent catalyst circulation pipe 2-10, a spent catalyst circulation slide valve 2-11, a spent catalyst inclined pipe 2-12, a methanol conversion reactor stripper 2-13, a spent catalyst slide valve 2-14, and a spent catalyst delivery pipe 2-15.

A lower part of the methanol conversion reactor 2 is a reaction zone II, a middle part thereof is a spent catalyst zone, and an upper part thereof is a gas-solid separation zone.

The methanol conversion reactor distributor 2-2 is located at a bottom of the reaction zone II of the methanol conversion reactor 2; the delivery pipe 2-3 is located in central zones of the middle and upper parts of the methanol conversion reactor 2; and a bottom end of the delivery pipe 2-3 is connected to a top end of the reaction zone II, and an upper part of the delivery pipe 2-3 is connected to an inlet of the first gas-solid separation unit 2-4 of the methanol conversion reactor.

The first gas-solid separation unit 2-4 of the methanol conversion reactor is located in the gas-solid separation zone of the methanol conversion reactor; and a gas outlet of the first gas-solid separation unit 2-4 of the methanol conversion reactor is connected to the methanol conversion reactor gas collection chamber 2-5, and a catalyst outlet of the first gas-solid separation unit 2-4 of the methanol conversion reactor is formed in the spent catalyst zone.

The spent catalyst zone gas distributor 2-6 is located at a bottom of the spent catalyst zone, and the methanol conversion reactor cooler 2-7 is located in the spent catalyst zone.

The second gas-solid separation unit 2-8 of the methanol conversion reactor is located in the gas-solid separation zone of the methanol conversion reactor; an inlet of the second gas-solid separation unit 2-8 of the methanol conversion reactor is formed in the gas-solid separation zone of the methanol conversion reactor, a gas outlet of the second gas-solid separation unit 2-8 of the methanol conversion reactor is connected to the methanol conversion reactor gas collection chamber 2-5, and a catalyst outlet of the second gas-solid separation unit 2-8 of the methanol conversion reactor is formed in the spent catalyst zone; the methanol conversion reactor gas collection chamber 2-5 is located at a top of the methanol conversion reactor 2, and the product gas delivery pipe 2-9 is connected to a top of the methanol conversion reactor gas collection chamber 2-5; an inlet of the spent catalyst circulation pipe 2-10 is connected to the spent catalyst zone, and an outlet of the spent catalyst circulation pipe 2-10 is connected to the bottom of the reaction zone II of the methanol conversion reactor; the spent catalyst circulation slide valve 2-11 is arranged in the spent catalyst circulation pipe 2-10; an outlet of the coke controlled catalyst delivery pipe 1-4 is connected to the bottom of the reaction zone II of the methanol conversion reactor 2, an inlet of the spent catalyst inclined pipe 2-12 is connected to the spent catalyst zone, and an outlet of the spent catalyst inclined pipe 2-12 is connected to an upper part of the methanol conversion reactor stripper 2-13; the methanol conversion reactor stripper 2-13 is arranged outside the methanol conversion reactor shell 2-1; and an inlet of the spent catalyst slide valve 2-14 is connected to a bottom of the methanol conversion reactor stripper 2-13 through a pipeline, an outlet of the spent catalyst slide valve 2-14 is connected to an inlet of the spent catalyst delivery pipe 2-15 through a pipeline, and an outlet of the spent catalyst delivery pipe 2-15 is connected to a middle part of the regenerator 3.

In a preferred embodiment, the first gas-solid separation unit 2-4 of the methanol conversion reactor may adopt one or more sets of gas-solid cyclone separators, and each set of gas-solid cyclone separators may include a first-stage gas-solid cyclone separator and a second-stage gas-solid cyclone separator.

In a preferred embodiment, the second gas-solid separation unit 2-8 of the methanol conversion reactor may adopt one or more sets of gas-solid cyclone separators, and each set of gas-solid cyclone separators may include a first-stage gas-solid cyclone separator and a second-stage gas-solid cyclone separator.

The methanol conversion reactor 2 may be a fluidized bed reactor.

The regenerator 3 includes a regenerator shell 3-1, a regenerator distributor 3-2, a regenerator gas-solid separation unit 3-3, a regenerator gas collection chamber 3-4, a flue gas delivery pipe 3-5, a regenerator stripper 3-6, a regenerator cooler 3-7, a regenerated catalyst slide valve 3-8, and a regenerated catalyst delivery pipe 3-9. The regenerator distributor 3-2 is located at a bottom of the regenerator 3, and the regenerator gas-solid separation unit 3-3 is located at an upper part of the regenerator 3; an inlet of the regenerator gas-solid separation unit 3-3 is formed at an upper part of the regenerator 3, a gas outlet of the regenerator gas-solid separation unit 3-3 is connected to the regenerator gas collection chamber 3-4, and a catalyst outlet of the regenerator gas-solid separation unit 3-3 is formed at a lower part of the regenerator 3; the regenerator gas collection chamber 3-4 is located at a top of the regenerator 3, and the flue gas delivery pipe 3-5 is connected to a top of the regenerator gas collection chamber 3-4; the regenerator stripper 3-6 is located outside the regenerator shell 3-1, and an inlet pipe of the regenerator stripper 3-6 penetrates through the regenerator shell 3-1 and is opened above the regenerator distributor 3-2; the regenerator cooler 3-7 is located in the regenerator stripper 3-6; and an inlet of the regenerated catalyst slide valve 3-8 is connected to a bottom of the regenerator stripper 3-6 through a pipeline, an outlet of the regenerated catalyst slide valve 3-8 is connected to an inlet of the regenerated catalyst delivery pipe 3-9 through a pipeline, and an outlet of the regenerated catalyst delivery pipe 3-9 is connected to the coke control reactor 1.

In a preferred embodiment, the regenerator gas-solid separation unit 3-3 may adopt one or more sets of gas-solid cyclone separators, and each set of gas-solid cyclone separators may include a first-stage gas-solid cyclone separator and a second-stage gas-solid cyclone separator.

The regenerator 3 may be a fluidized bed reactor.

The present application also provides an MTO method including the method for on-line modification of a DMTO catalyst through a coke control reaction, including the following steps:

a. a coke control raw material is fed into the reaction zone I of the coke control reactor 1 from the coke control reactor distributor 1-2, and a regenerated catalyst is fed into the reaction zone I of the coke control reactor 1 from the regenerated catalyst delivery pipe 3-9, where in the reaction zone I of the coke control reactor 1, the coke control raw material contacts the regenerated catalyst to allow a chemical reaction to generate a coke controlled catalyst and a coke control product gas; the coke controlled catalyst passes through the m reaction zone I subzones in sequence through the catalyst circulation holes on the baffles 1-3, and then enters the reaction zone II of the methanol conversion reactor 2 through the coke controlled catalyst delivery pipe 1-4 and the coke controlled catalyst slide valve 1-5; and the coke control product gas enters the gas-solid separation zone of the methanol conversion reactor 2 through the coke control product gas delivery pipe 1-6;

b. a raw material with an oxygen-containing compound is fed into the reaction zone II of the methanol conversion reactor from the methanol conversion reactor distributor 2-2, and contacts the coke controlled catalyst to generate a stream A with low-carbon olefins and a spent catalyst; the stream A enters the first gas-solid separation unit 2-4 of the methanol conversion reactor through the delivery pipe 2-3 to undergo gas-solid separation to obtain a gas-phase stream B and a solid-phase stream C, where the gas-phase stream B is a gas with low-carbon olefins and the solid-phase stream C is a spent catalyst; the gas-phase stream B enters the methanol conversion reactor gas collection chamber 2-5, and the solid-phase stream C enters the spent catalyst zone; a spent catalyst zone fluidizing gas is fed into the spent catalyst zone from the spent catalyst zone gas distributor 2-6 and contacts the spent catalyst, and the spent catalyst zone fluidizing gas and the coke control product gas are mixed and carry a part of the spent catalyst to produce a stream D; the stream D enters the second gas-solid separation unit 2-8 of the methanol conversion reactor to undergo gas-solid separation to obtain a gas-phase stream E and a solid-phase stream F, where the gas-phase stream E is a mixed gas of the spent catalyst zone fluidizing gas and the coke control product gas and the solid-phase stream F is the spent catalyst; the gas-phase stream E enters the methanol conversion reactor gas collection chamber (2-5), and the solid-phase stream F enters the spent catalyst zone; the gas-phase stream B and the gas-phase stream E are mixed in the methanol conversion reactor gas collection chamber (2-5) to produce a product gas, and the product gas enters a downstream working section through the product gas delivery pipe 2-9; a part of the spent catalyst in the spent catalyst zone is returned to a bottom of the reaction zone II of the methanol conversion reactor 2 through the spent catalyst circulation pipe 2-10 and the spent catalyst circulation slide valve 2-11, and the remaining part of the spent catalyst enters the methanol conversion reactor stripper 2-13 through the spent catalyst inclined pipe 2-12 to undergo stripping, and then enters a middle part of the regenerator 3 through the spent catalyst slide valve 2-14 and the spent catalyst delivery pipe 2-15; and c. a regeneration gas is fed from the regenerator distributor 3-2 to the bottom of the regenerator, and in the regenerator, the regeneration gas contacts the spent catalyst to allow a chemical reaction, such that a part of coke in the spent catalyst is burned and eliminated to generate a stream G with a flue gas and a regenerated catalyst; the stream G enters the regenerator gas-solid separation unit 3-3 to undergo gas-solid separation to obtain a flue gas and a regenerated catalyst; the flue gas enters the regenerator gas collection chamber 3-4, and then enters a downstream flue gas treatment system through the flue gas delivery pipe 3-5; the regenerated catalyst is returned to the bottom of the regenerator 3; and the regenerated catalyst in the regenerator 3 enters the regenerator stripper 3-6 to be stripped and cooled, and then enters the coke control reactor 1 through the regenerated catalyst slide valve 3-8 and the regenerated catalyst delivery pipe 3-9.

In the method of the present application, the product gas may be composed of 37 wt % to 60 wt % of ethylene, 33 wt % to 57 wt % of propylene, less than or equal to 5 wt % of $C_4$-$C_6$ hydrocarbon compounds, and less than or equal to 4 wt % of other components; and the other components may be methane, ethane, propane, hydrogen, CO, $CO_2$, and the like, and the total selectivity of ethylene and propylene in the product gas may be 93 wt % to 96 wt %.

In the present application, when the unit consumption of production is expressed, a mass of DME in the oxygen-containing compound is equivalently converted into a mass of methanol based on a mass of the element C, and a unit of the unit consumption of production is ton of methanol/ton of low-carbon olefins.

In the method of the present application, the unit consumption of production may be 2.50 to 2.58 tons of methanol/ton of low-carbon olefins.

In order to well illustrate the present application and facilitate the understanding of the technical solutions of the present application, typical but non-limiting examples of the present application are as follows:

Example 1

In this example, the device shown in FIG. 1 is adopted, where a cross section of the reaction zone I of the coke control reactor 1 is rectangular; a cross section of the reaction zone I subzone is rectangular; n=1 and m=2; and the $1^{st}$ and $2^{nd}$ reaction zone I subzones are arranged from left to right in sequence.

In this example, the coke control raw material is a mixture of 6 wt % of butane, 81 wt % of butene, 2 wt % of methanol, and 11 wt % of water; the oxygen-containing compound is methanol; the spent catalyst zone fluidizing gas is nitrogen; the regeneration gas is air; an active component in the catalyst is an SAPO-34 molecular sieve; a coke content in the regenerated catalyst is about 1 wt %; a coke content in the coke controlled catalyst is about 4 wt %, where a total mass of polymethylbenzene and polymethylnaphthalene accounts for about 86 wt % of a total mass of coke, a mass of coke species with a molecular weight greater than 184 accounts for about 11 wt % of a total mass of coke, and a quartile deviation of coke content distribution in the coke controlled catalyst is about 0.9 wt %; a coke content in the spent catalyst is about 9 wt %; process operating conditions of the reaction zone I of the coke control reactor 1 are as follows: apparent gas linear velocity: about 0.3 m/s, reaction temperature: about 500° C., reaction pressure: about 100 kPa, and bed density: about 600 kg/m$^3$; process operating conditions of the reaction zone II of the methanol conversion reactor 2 are as follows: apparent gas linear velocity: about 7.0 m/s, reaction temperature: about 550° C., reaction pressure: about 100 kPa, and bed density: about 100 kg/m$^3$; process operating conditions of the spent catalyst zone of the methanol conversion reactor 2 are as follows: apparent gas linear velocity: about 1.0 m/s, reaction temperature: about 550° C., reaction pressure: about 100 kPa, and bed density: about 200 kg/m$^3$; and process operating conditions of the regenerator 3 are as follows: apparent gas linear velocity: about 0.5 m/s, regeneration temperature: about 750° C., regeneration pressure: about 100 kPa, and bed density: about 700 kg/m$^3$.

In this example, a WHSV of the oxygen-containing compound in the methanol conversion reactor is about 20 h$^{-1}$; the product gas is composed of 60 wt % of ethylene, 33 wt % of propylene, 3 wt % of $C_4$-$C_6$ hydrocarbon compounds, and 4 wt % of other components, where the other components include methane, ethane, propane, hydrogen, CO, $CO_2$, and the like; and the unit consumption of production is 2.58 tons of methanol/ton of low-carbon olefins.

Example 2

In this example, the device shown in FIG. 1 is adopted, where a cross section of the reaction zone I of the coke control reactor 1 is rectangular; a cross section of the reaction zone I subzone is rectangular; n=9 and m=10; and the $1^{st}$ to $10^{th}$ reaction zone I subzones are arranged from left to right in sequence.

In this example, the coke control raw material is a mixture of 22 wt % of methane, 24 wt % of ethane, 3 wt % of ethylene, 28 wt % of propane, 4 wt % of propylene, 7 wt % of hydrogen, and 12 wt % of water; the oxygen-containing compound is a mixture of 82 wt % of methanol and 18 wt % of DME; the spent catalyst zone fluidizing gas is water vapor; the regeneration gas is air; an active component in the catalyst is an SAPO-34 molecular sieve; a coke content in the regenerated catalyst is about 3 wt %; a coke content in the coke controlled catalyst is about 9 wt %, where a total mass of polymethylbenzene and polymethylnaphthalene accounts for about 70 wt % of a total mass of coke, a mass of coke species with a molecular weight greater than 184 accounts for about 25 wt % of a total mass of coke, and a quartile deviation of coke content distribution in the coke controlled catalyst is about 0.2 wt %; a coke content in the spent catalyst is about 13 wt %; process operating conditions of the reaction zone I of the coke control reactor 1 are as follows: apparent gas linear velocity: about 0.2 m/s, reaction temperature: about 300° C., reaction pressure: about 500 kPa, and bed density: about 700 kg/m$^3$; process operating conditions of the reaction zone II of the methanol conversion reactor 2 are as follows: apparent gas linear velocity: about 0.5 m/s, reaction temperature: about 350° C., reaction pressure: about 500 kPa, and bed density: about 500 kg/m$^3$; process operating conditions of the spent catalyst zone of the methanol conversion reactor 2 are as follows: apparent gas linear velocity: about 0.1 m/s, reaction temperature: about 350° C., reaction pressure: about 500 kPa, and bed density: about 800 kg/m$^3$; and process operating conditions of the regenerator 3 are as follows: apparent gas linear velocity: about 2.0 m/s, regeneration temperature: about 600° C., regeneration pressure: about 500 kPa, and bed density: about 150 kg/m$^3$.

In this example, a WHSV of the oxygen-containing compound in the methanol conversion reactor is about 5 h$^{-1}$; the product gas is composed of 37 wt % of ethylene, 57 wt % of propylene, 5 wt % of $C_4$-$C_6$ hydrocarbon compounds, and 1 wt % of other components, where the other components include methane, ethane, propane, hydrogen, CO, $CO_2$, and the like; and the unit consumption of production is 2.55 tons of methanol/ton of low-carbon olefins.

Example 3

In this example, the device shown in FIG. 1 is adopted, where a structure of the coke control reactor 1 is shown in FIG. 2; a cross section of the reaction zone I of the coke control reactor of this example is circular, and a cross section of a reaction zone I subzone is fan-shaped; n=4 and m=4; and the $1^{st}$ to $4^{th}$ reaction zone I subzones are arranged concentrically in a counterclockwise direction, and a baffle 1-3 shared by the $1^{st}$ reaction zone I subzone and the $4^{th}$ reaction zone I subzone of the coke control reactor does not have catalyst circulation holes.

In this example, the coke control raw material is a mixture of 1 wt % of propane, 1 wt % of propylene, 3 wt % of butane, 51 wt % of butene, 3 wt % of pentane, 22 wt % of pentene, 1 wt % of hexane, 7 wt % of hexene, 2 wt % of methanol, and 9 wt % of water; the oxygen-containing compound is DME; the spent catalyst zone fluidizing gas is nitrogen; the regeneration gas is a mixture of 50 wt % of air and 50 wt % of oxygen; an active component in the catalyst is an SAPO-34 molecular sieve; a coke content in the regenerated catalyst is about 1 wt %; a coke content in the coke controlled catalyst is about 6 wt %, where a total mass of polymethylbenzene and polymethylnaphthalene accounts for about 80 wt % of a total mass of coke, a mass of coke species with a molecular weight greater than 184 accounts for about 14 wt % of a total mass of coke, and a quartile deviation of coke content distribution in the coke controlled catalyst is about 0.5 wt %; a coke content in the spent catalyst is about 11 wt %; process operating conditions of the reaction zone I of the coke control reactor 1 are as follows: apparent gas linear velocity: about 0.4 m/s, reaction temperature: about 700° C., reaction pressure: about 300 kPa, and bed density: about 500 kg/m$^3$; process operating conditions of the reaction zone II of the methanol conversion reactor 2 are as follows: apparent gas linear velocity: about 3.0 m/s, reaction temperature: about 450° C., reaction pressure: about 300 kPa, and bed density: about 230 kg/m$^3$; process operating conditions of the spent catalyst zone of the methanol conversion reactor 2 are as follows: apparent gas linear velocity: about 0.2 m/s, reaction temperature: about 450° C., reaction pressure: about 300 kPa, and bed density: about 600 kg/m$^3$; and process operating conditions of the regenerator 3 are as follows: apparent gas linear velocity: about 1.0 m/s, regeneration temperature: about 750° C., regeneration pressure: about 300 kPa, and bed density: about 360 kg/m$^3$.

In this example, a WHSV of the oxygen-containing compound in the methanol conversion reactor is about 9 h$^{-1}$; the product gas is composed of 51 wt % of ethylene, 43 wt % of propylene, 2 wt % of $C_4$-$C_6$ hydrocarbon compounds, and 4 wt % of other components, where the other components include methane, ethane, propane, hydrogen, CO, $CO_2$, and the like; and the unit consumption of production is 2.55 tons of methanol/ton of low-carbon olefins.

Example 4

In this example, the device shown in FIG. 1 is adopted, where a structure of the coke control reactor 1 is shown in FIG. 2; a cross section of the reaction zone I of the coke control reactor of this example is circular, and a cross section of a reaction zone I subzone is fan-shaped; n=6 and m=6; and the $1^{st}$ to $6^{th}$ reaction zone I subzones are arranged concentrically in a counterclockwise direction, and a baffle 1-3 shared by the $1^{st}$ reaction zone I subzone and the $6^{th}$ reaction zone I subzone of the coke control reactor does not have catalyst circulation holes.

In this example, the coke control raw material is a mixture of 5 wt % of butane, 72 wt % of butene, 8 wt % of methanol, and 15 wt % of water; the oxygen-containing compound is methanol; the spent catalyst zone fluidizing gas is water vapor; the regeneration gas is a mixture of 50 wt % of air and 50 wt % of nitrogen; an active component in the catalyst is an SAPO-34 molecular sieve; a coke content in the regenerated catalyst is about 2 wt %; a coke content in the coke controlled catalyst is about 6 wt %, where a total mass of polymethylbenzene and polymethylnaphthalene accounts for about 82 wt % of a total mass of coke, a mass of coke species with a molecular weight greater than 184 accounts for about 13 wt % of a total mass of coke, and a quartile deviation of coke content distribution in the coke controlled catalyst is about 0.3 wt %; a coke content in the spent catalyst is about 12 wt %; process operating conditions of the reaction zone I of the coke control reactor 1 are as follows: apparent gas linear velocity: about 0.5 m/s, reaction temperature: about 600° C., reaction pressure: about 200 kPa, and bed density: about 400 kg/m$^3$; process operating conditions of the reaction zone II of the methanol conversion reactor 2 are as follows: apparent gas linear velocity: about 4.0 m/s, reaction temperature: about 500° C., reaction pressure: about 200 kPa, and bed density: about 160 kg/m$^3$; process operating conditions of the spent catalyst zone of the methanol conversion reactor 2 are as follows: apparent gas linear velocity: about 0.5 m/s, reaction temperature: about 500° C., reaction pressure: about 200 kPa, and bed density: about 300 kg/m$^3$; and process operating conditions of the regenerator 3 are as follows: apparent gas linear velocity: about 1.5 m/s, regeneration temperature: about 650° C., regeneration pressure: about 200 kPa, and bed density: about 280 kg/m$^3$.

In this example, a WHSV of the oxygen-containing compound in the methanol conversion reactor is about 13 h$^{-1}$; the product gas is composed of 53 wt % of ethylene, 42 wt % of propylene, 4 wt % of $C_4$-$C_6$ hydrocarbon compounds, and 1 wt % of other components, where the other components include methane, ethane, propane, hydrogen, CO, $CO_2$, and the like; and the unit consumption of production is 2.52 tons of methanol/ton of low-carbon olefins.

Example 5

In this example, the device shown in FIG. 1 is adopted, where a structure of the coke control reactor 1 is shown in FIG. 3; a cross section of the reaction zone I of the coke control reactor of this example is annular, and a cross section of a reaction zone I subzone is sector-annular; n=6 and m=6; and the 1$^{st}$ to 6$^{th}$ reaction zone I subzones are arranged concentrically in a clockwise direction, and a baffle 1-3 shared by the 1$^{st}$ reaction zone I subzone and the 6$^{th}$ reaction zone I subzone of the coke control reactor does not have catalyst circulation holes.

In this example, the coke control raw material is a mixture of 34 wt % of pentane, 46 wt % of pentene, 3 wt % of ethanol, and 17 wt % of water; the oxygen-containing compound is methanol; the spent catalyst zone fluidizing gas is a mixture of 5 wt % of nitrogen and 95 wt % of water vapor; the regeneration gas is a mixture of 50 wt % of air and 50 wt % of water vapor; an active component in the catalyst is an SAPO-34 molecular sieve; a coke content in the regenerated catalyst is about 2 wt %; a coke content in the coke controlled catalyst is about 7 wt %, where a total mass of polymethylbenzene and polymethylnaphthalene accounts for about 74 wt % of a total mass of coke, a mass of coke species with a molecular weight greater than 184 accounts for about 10 wt % of a total mass of coke, and a quartile deviation of coke content distribution in the coke controlled catalyst is about 0.3 wt %; a coke content in the spent catalyst is about 12 wt %; process operating conditions of the reaction zone I of the coke control reactor 1 are as follows: apparent gas linear velocity: about 0.4 m/s, reaction temperature: about 400° C., reaction pressure: about 300 kPa, and bed density: about 500 kg/m$^3$; process operating conditions of the reaction zone II of the methanol conversion reactor 2 are as follows: apparent gas linear velocity: about 3.0 m/s, reaction temperature: about 400° C., reaction pressure: about 300 kPa, and bed density: about 230 kg/m$^3$; process operating conditions of the spent catalyst zone of the methanol conversion reactor 2 are as follows: apparent gas linear velocity: about 0.3 m/s, reaction temperature: about 400° C., reaction pressure: about 300 kPa, and bed density: about 450 kg/m$^3$; and process operating conditions of the regenerator 3 are as follows: apparent gas linear velocity: about 0.8 m/s, regeneration temperature: about 680° C., regeneration pressure: about 300 kPa, and bed density: about 500 kg/m$^3$.

In this example, a WHSV of the oxygen-containing compound in the methanol conversion reactor is about 9 h$^{-1}$; the product gas is composed of 41 wt % of ethylene, 55 wt % of propylene, 2 wt % of $C_4$-$C_6$ hydrocarbon compounds, and 2 wt % of other components, where the other components include methane, ethane, propane, hydrogen, CO, $CO_2$, and the like; and the unit consumption of production is 2.50 tons of methanol/ton of low-carbon olefins.

Example 6

In this example, the device shown in FIG. 1 is adopted, where a structure of the coke control reactor 1 is shown in FIG. 3; a cross section of the reaction zone I of the coke control reactor of this example is annular, and a cross section of a reaction zone I subzone is sector-annular; n=9 and m=9; and the 1$^{st}$ to 9$^{th}$ reaction zone I subzones are arranged concentrically in a clockwise direction, and a baffle 1-3 shared by the 1$^{st}$ reaction zone I subzone and the 9$^{th}$ reaction zone I subzone of the coke control reactor does not have catalyst circulation holes.

In this example, the coke control raw material is a mixture of 26 wt % of hexane, 23 wt % of hexene, 2 wt % of methanol, 1 wt % of ethanol, and 48 wt % of water; the oxygen-containing compound is methanol; the spent catalyst zone fluidizing gas is a mixture of 73 wt % of nitrogen and 27 wt % of water vapor; the regeneration gas is a mixture of 85 wt % of air, 12 wt % of water vapor, and 3 wt % of nitrogen; an active component in the catalyst is an SAPO-34 molecular sieve; a coke content in the regenerated catalyst is about 3 wt %; a coke content in the coke controlled catalyst is about 8 wt %, where a total mass of polymethylbenzene and polymethylnaphthalene accounts for about 79 wt % of a total mass of coke, a mass of coke species with a molecular weight greater than 184 accounts for about 17 wt % of a total mass of coke, and a quartile deviation of coke content distribution in the coke controlled catalyst is about 0.1 wt %; a coke content in the spent catalyst is about 12 wt %; process operating conditions of the reaction zone I of the coke control reactor 1 are as follows: apparent gas linear velocity: about 0.1 m/s, reaction temperature: about 650° C., reaction pressure: about 400 kPa, and bed density: about 800 kg/m$^3$; process operating conditions of the reaction zone II of the methanol conversion reactor 2 are as follows: apparent gas linear velocity: about 2.0 m/s, reaction temperature: about 500° C., reaction pressure: about 400 kPa, and bed density: about 350 kg/m$^3$; process operating conditions of the spent catalyst zone of the methanol conversion reactor 2 are as follows: apparent gas linear velocity: about 0.3 m/s, reaction temperature: about 500° C., reaction pressure: about 400 kPa, and bed density: about 450 kg/m$^3$; and process operating conditions of the regenerator 3 are as follows: apparent gas linear velocity: about 0.8 m/s, regeneration temperature: about 700° C., regeneration pressure: about 400 kPa, and bed density: about 500 kg/m$^3$.

In this example, a WHSV of the oxygen-containing compound in the methanol conversion reactor is about 7 h$^{-1}$;

the product gas is composed of 50 wt % of ethylene, 43 wt % of propylene, 4 wt % of $C_4$-$C_6$ hydrocarbon compounds, and 3 wt % of other components, where the other components include methane, ethane, propane, hydrogen, CO, $CO_2$, and the like; and the unit consumption of production is 2.58 tons of methanol/ton of low-carbon olefins.

COMPARATIVE EXAMPLE

This example is a comparative example and is different from Example 5 in that, the coke control reaction is not used for on-line modification of the DMTO catalyst; and the raw material fed into the coke control reactor is nitrogen, which is an inert gas and does not change the properties of the regenerated catalyst in the coke control reactor, that is, a catalyst entering the reaction zone II of the methanol conversion reactor is the regenerated catalyst.

In this example, the product gas is composed of 36 wt % of ethylene, 44 wt % of propylene, 13 wt % of $C_4$-$C_6$ hydrocarbon compounds, and 7 wt % of other components, where the other components include methane, ethane, propane, hydrogen, CO, $CO_2$, and the like; and the unit consumption of production is 2.99 tons of methanol/ton of low-carbon olefins.

This comparative example shows that the on-line modification of a DMTO catalyst through a coke control reaction can greatly improve the performance of the catalyst and reduce the unit consumption of production.

The above examples are merely few examples of the present application, and do not limit the present application in any form. Although the present application is disclosed as above with preferred examples, the present application is not limited thereto. Some changes or modifications made by any technical personnel familiar with the profession using the technical content disclosed above without departing from the scope of the technical solutions of the present application are equivalent to equivalent implementation cases and fall within the scope of the technical solutions.

What is claimed is:

1. A coke control reactor, wherein the coke control reactor comprises a coke control reactor shell, a first reaction zone, and a coke controlled catalyst settling zone;
    the coke control reactor shell comprises an upper coke control reactor shell and a lower coke control reactor shell; the upper coke control reactor shell encloses the coke controlled catalyst settling zone;
    the lower coke control reactor shell encloses the first reaction zone;
    the first reaction zone communicates with the coke controlled catalyst settling zone;
    a cross-sectional area at any position of the first reaction zone is less than a cross-sectional area at any position of the coke controlled catalyst settling zone;
    n baffles are arranged in a vertical direction in the first reaction zone, bottoms of the n baffles are connected to a bottom of the coke control reactor, tops of the n baffles are located in the coke controlled catalyst settling zone, and the n baffles divide the first reaction zone into m subzones of the first reaction zone, wherein m and n are both integers; and
    a catalyst circulation hole is formed in each of the n baffles, such that a catalyst flows in the first reaction zone.

2. The coke control reactor according to claim 1, wherein $1 \leq n \leq 9$; and $2 \leq m \leq 10$;
    wherein a cross section of the first reaction zone and a cross section of each of the m subzones are all rectangular; the catalyst circulation hole is formed in each of the n baffles; and the catalyst circulation holes on two adjacent baffles are staggered up and down, such that the catalyst flows in the first reaction zone;
    wherein the cross section of the first reaction zone is circular; the cross section of each of the m subzones is fan-shaped; and at least one catalyst circulation hole is formed in each of n−1 of the n baffles, such that the catalyst flows in the first reaction zone in an annular manner; or
    wherein the cross section of the first reaction zone is annular; the cross section of each of the m subzones is fan-shaped; and at least one catalyst circulation hole is formed in each of n−1 of the n baffles, such that the catalyst flows in the first reaction zone in the annular manner.

3. The coke control reactor according to claim 1, wherein a cross-sectional area of the coke controlled catalyst settling zone is 1.5 to 3 times a cross-sectional area of the first reaction zone; and
    wherein the coke control reactor is a bubbling fluidized bed reactor.

4. The coke control reactor according to claim 1, wherein the coke control reactor further comprises a transition zone;
    the transition zone is located between the first reaction zone and the coke controlled catalyst settling zone;
    a cross-sectional area at any position of the transition zone is between the cross-sectional area at any position of the first reaction zone and the cross-sectional area at any position of the coke controlled catalyst settling zone; and
    the transition zone, the first reaction zone, and the coke controlled catalyst settling zone communicate with each other coaxially.

5. The coke control reactor according to claim 1, wherein the first reaction zone comprises a catalyst inlet, a coke controlled catalyst outlet, and a coke control raw material inlet;
    the m subzones of the first reaction zone comprise a first subzone, and a second subzone to an $m^{th}$ subzone; the catalyst inlet is formed in the first subzone; the coke controlled catalyst outlet is formed in the $m^{th}$ subzone;
    the coke control raw material inlet is formed at a bottom of each of m subzones;
    the coke controlled catalyst settling zone comprises a coke control gas outlet; and the coke control gas outlet is formed at a top of the coke controlled catalyst settling zone;
    wherein a coke control reactor distributor is provided at the coke control raw material inlet.

6. A device for preparing low-carbon olefins from an oxygen-containing compound, wherein the device comprises a methanol conversion reactor and the coke control reactor according to claim 1.

7. The device according to claim 6, wherein the methanol conversion reactor comprises a methanol conversion reactor shell and a delivery pipe;
    the methanol conversion reactor shell comprises a lower methanol conversion reactor shell and an upper methanol conversion reactor shell;
    the lower methanol conversion reactor shell encloses a second reaction zone;
    the delivery pipe is located above the second reaction zone; the delivery pipe has a first end closed and a second end communicating with the second reaction zone;

the upper methanol conversion reactor shell is arranged on a periphery of the delivery pipe;

the upper methanol conversion reactor shell and a pipe wall of the delivery pipe enclose a cavity;

the cavity is divided into a spent catalyst zone and a gas-solid separation zone from bottom to top, respectively; and the spent catalyst zone is provided with a spent catalyst zone gas distributor;

wherein the gas-solid separation zone is provided with a first gas-solid separation unit of the methanol conversion reactor; an upper part of the delivery pipe is connected to an inlet of the first gas-solid separation unit of the methanol conversion reactor; a spent catalyst outlet of the first gas-solid separation unit of the methanol conversion reactor is formed in the spent catalyst zone; a gas outlet of the first gas-solid separation unit of the methanol conversion reactor communicates with a methanol conversion reactor gas collection chamber; and the methanol conversion reactor gas collection chamber communicates with a product gas delivery pipe;

wherein the gas-solid separation zone is further provided with a second gas-solid separation unit of the methanol conversion reactor; a gas inlet of the second gas-solid separation unit of the methanol conversion reactor is formed in the gas-solid separation zone; a spent catalyst outlet of the second gas-solid separation unit of the methanol conversion reactor is formed in the spent catalyst zone; and a gas outlet of the second gas-solid separation unit of the methanol conversion reactor communicates with the methanol conversion reactor gas collection chamber.

8. The device according to claim 7, wherein the spent catalyst zone gas distributor is located below the first gas-solid separation unit of the methanol conversion reactor and the second gas-solid separation unit of the methanol conversion reactor.

9. The device according to claim 7, wherein a spent catalyst circulation pipe and a spent catalyst inclined pipe are further arranged outside the spent catalyst zone;

the spent catalyst circulation pipe is configured to connect the spent catalyst zone and the second reaction zone; and the spent catalyst inclined pipe is configured to output a spent catalyst.

10. The device according to claim 7, wherein the second reaction zone communicates with the first reaction zone through a coke controlled catalyst delivery pipe.

11. The device according to claim 9, wherein the device further comprises a regenerator;

the regenerator is connected to the spent catalyst inclined pipe, such that the spent catalyst is able to be delivered to the regenerator;

the regenerator is connected to a regenerated catalyst delivery pipe, such that a regenerated catalyst is able to be delivered to the coke control reactor; and an inner bottom of the regenerator is provided with a regenerator distributor;

wherein a bottom of the regenerator is further provided with a regenerator stripper; an upper section of the regenerator stripper is arranged inside the regenerator, and an inlet of the upper section of the regenerator stripper is formed above the regenerator distributor; and a lower section of the regenerator stripper is arranged outside the regenerator, and an outlet of the lower section of the regenerator stripper is connected to the regenerated catalyst delivery pipe;

wherein the regenerator is connected to the spent catalyst inclined pipe through a spent catalyst delivery pipe and a methanol conversion reactor stripper; and the regenerator is connected to the regenerated catalyst delivery pipe through the regenerator stripper;

wherein the regenerator is further provided with a regenerator gas-solid separation unit and a regenerator gas collection chamber; a regenerated catalyst outlet of the regenerator gas-solid separation unit is formed above the regenerator distributor; a gas outlet of the regenerator gas-solid separation unit is connected to the regenerator gas collection chamber; and the regenerator gas collection chamber is connected to a flue gas delivery pipe located outside the regenerator.

12. A method for preparing low-carbon olefins from an oxygen-containing compound, comprising a method for on-line modification of a dimethyl ether/methanol to olefins (DMTO) catalyst using the coke regulation reactor according to claim 1.

13. The method according to claim 12, wherein the method further comprises:

feeding a coke control product gas into a gas-solid separation zone of a methanol conversion reactor; and feeding a coke controlled catalyst into a second reaction zone of the methanol conversion reactor;

wherein in the second reaction zone, a raw material with the oxygen-containing compound contacts and reacts with the coke controlled catalyst to generate a first stream with low-carbon olefins and a spent catalyst;

wherein the first stream is separated into a first gas-phase stream and a first solid-phase stream after being subjected to gas-solid separation in the gas-solid separation zone of the methanol conversion reactor; the first gas-phase stream enters a methanol conversion reactor gas collection chamber; the first solid-phase stream enters a spent catalyst zone; and the first gas-phase stream comprises the low-carbon olefins, and the first solid-phase stream comprises the spent catalyst;

wherein a spent catalyst zone fluidizing gas is fed into the spent catalyst zone; the spent catalyst zone fluidizing gas and the coke control product gas are mixed and carry a part of the spent catalyst to produce a second stream; the second stream is separated into a second gas-phase stream and a second solid-phase stream after being subjected to gas-solid separation; the second gas-phase stream enters the methanol conversion reactor gas collection chamber; the second solid-phase stream enters the spent catalyst zone; the second gas-phase stream is a mixed gas of the spent catalyst zone fluidizing gas and the coke control product gas; and the second solid-phase stream is the spent catalyst;

wherein the first gas-phase stream and the second gas-phase stream are mixed in the methanol conversion reactor gas collection chamber to produce a product gas, and the product gas enters a downstream working section through a product gas delivery pipe;

wherein a part of the spent catalyst in the spent catalyst zone is returned to a bottom of the second reaction zone through a spent catalyst circulation pipe; and a remaining part of the spent catalyst is discharged through a spent catalyst inclined pipe;

wherein the remaining part of the spent catalyst discharged through the spent catalyst inclined pipe is fed into a regenerator; and a regeneration gas is fed into the regenerator to contact and react with the spent catalyst to obtain a third stream with a flue gas and a regenerated catalyst;

wherein the third stream is subjected to gas-solid separation; a separated flue gas enters a regenerator gas collection chamber, and then enters a downstream flue gas treatment system through a flue gas delivery pipe; and a separated regenerated catalyst is stripped and cooled, and then enters a coke control reactor.

14. The method according to claim 13, wherein the oxygen-containing compound comprises methanol and/or dimethyl ether (DME);

wherein a coke content in the spent catalyst is 9 wt % to 13 wt %.

15. The method according to claim 13, wherein the spent catalyst zone fluidizing gas comprises nitrogen and/or water vapor;

wherein the regeneration gas comprises 0 wt % to 100 wt % of air, 0 wt % to 50 wt % of oxygen, 0 wt % to 50 wt % of nitrogen, and 0 wt % to 50 wt % of water vapor.

16. The method according to claim 13, wherein process operating conditions of the second reaction zone of the methanol conversion reactor are as follows: apparent gas linear velocity: 0.5 m/s to 7.0 m/s; reaction temperature: 350° C. to 550° C.; reaction pressure: 100 kPa to 500 kPa; and bed density: 100 kg/m$^3$ to 500 kg/m$^3$;

wherein process operating conditions of the spent catalyst zone of the methanol conversion reactor are as follows: apparent gas linear velocity: 0.1 m/s to 1.0 m/s; reaction temperature: 350° C. to 550° C.; reaction pressure: 100 kPa to 500 kPa; and bed density: 200 kg/m$^3$ to 800 kg/m$^3$.

17. The method according to claim 13, wherein process operating conditions of the regenerator are as follows: apparent gas linear velocity: 0.5 m/s to 2.0 m/s; regeneration temperature: 600° C. to 750° C.; regeneration pressure: 100 kPa to 500 kPa; and bed density: 150 kg/m$^3$ to 700 kg/m$^3$.

18. The method according to claim 12, wherein the method for on-line modification of the DMTO catalyst at least comprises feeding a catalyst and a coke control raw material into the first reaction zone to allow a reaction to generate a product with a coke controlled catalyst;

wherein the catalyst flows through the catalyst circulation holes on the n baffles;

wherein the coke control raw material comprises $C_1$-$C_6$ hydrocarbon compounds;

wherein the $C_1$-$C_6$ hydrocarbon compounds are at least one selected from the group consisting of $C_1$-$C_6$ alkanes and $C_1$-$C_6$ olefins;

wherein the coke control raw material further comprises at least one from the group consisting of hydrogen, alcohol compound, and water; and a proportion of a total mass of the alcohol compound and the water in a mass of the coke control raw material is greater than or equal to 10% and less than or equal to 50%;

wherein the alcohol compound is at least one selected from the group consisting of methanol and ethanol;

wherein the coke control raw material comprises 0 wt % to 20 wt % of hydrogen, 0 wt % to 50 wt % of methane, 0 wt % to 50 wt % of ethane, 0 wt % to 20 wt % of ethylene, 0 wt % to 50 wt % of propane, 0 wt % to 20 wt % of propylene, 0 wt % to 90 wt % of butane, 0 wt % to 90 wt % of butene, 0 wt % to 90 wt % of pentane, 0 wt % to 90 wt % of pentene, 0 wt % to 90 wt % of hexane, 0 wt % to 90 wt % of hexene, 0 wt % to 50 wt % of methanol, 0 wt % to 50 wt % of ethanol, and 0 wt % to 50 wt % of water; and a content of the hydrocarbon compounds is greater than 0%.

19. The method according to claim 18, wherein the catalyst comprises an SAPO-34 molecular sieve; a coke content in the catalyst is less than or equal to 3 wt %;

a coke content in the coke controlled catalyst is 4 wt % to 9 wt %;

a quartile deviation of a coke content distribution in the coke controlled catalyst is less than 1 wt %;

coke species in the coke controlled catalyst comprise polymethylbenzene and polymethylnaphthalene;

a total mass of the polymethylbenzene and the polymethylnaphthalene accounts for greater than or equal to 70 wt % of a total mass of coke;

a mass of coke species with a molecular weight greater than 184 accounts for less than or equal to 25 wt % of the total mass of coke; and the total mass of the coke refers to a total mass of the coke species.

20. The method according to claim 18, wherein process operating conditions of the first reaction zone of the coke control reactor are as follows: apparent gas linear velocity: 0.1 m/s to 0.5 m/s; reaction temperature: 300° C. to 700° C.; reaction pressure: 100 kPa to 500 kPa; and bed density: 400 kg/m$^3$ to 800 kg/m$^3$;

wherein the method comprises: feeding a coke control raw material and the catalyst into the first reaction zone to allow a reaction to generate a coke controlled catalyst and a coke control product gas; allowing the coke controlled catalyst to pass through the m subzones of the first reaction zone in sequence through the catalyst circulation holes on the n baffles and then flow out through a coke controlled catalyst outlet; and allowing the coke control product gas to flow out through a coke control gas outlet.

* * * * *